United States Patent [19]
Lindberg et al.

[11] Patent Number: 5,370,666
[45] Date of Patent: Dec. 6, 1994

[54] PACEMAKER WITH POWER-CONSUMING COMPONENT INHIBITED DURING STORAGE

[75] Inventors: Jan Lindberg, Kista; Peter Andersson; Goran-Sven Budgifvars, both of Stockholm; Josef Vock, Spanga, all of Sweden

[73] Assignee: Siemens-Elema AB, Solna, Sweden

[21] Appl. No.: 73,331

[22] Filed: Jun. 7, 1993

[30] Foreign Application Priority Data

Jun. 5, 1992 [SE] Sweden ............... 9201745

[51] Int. Cl.⁵ .................................... A61N 1/372
[52] U.S. Cl. ............................. 607/16; 607/30; 607/60; 607/37; 607/32; 607/34; 128/734
[58] Field of Search .......... 607/30, 60, 37, 32, 607/34, 27, 2, 16; 128/734

[56] References Cited

U.S. PATENT DOCUMENTS

| | | | |
|---|---|---|---|
| 3,195,540 | 7/1965 | Waller | 607/36 |
| 3,198,195 | 8/1965 | Chardack | 607/30 |
| 3,738,369 | 6/1973 | Adams et al. | |
| 4,066,086 | 1/1978 | Alferness et al. | 607/30 |
| 4,345,604 | 8/1982 | Renirie | |
| 4,884,575 | 12/1989 | Sanders | 607/30 |
| 5,003,975 | 4/1991 | Hafelfinger et al. | 607/28 |

FOREIGN PATENT DOCUMENTS

| | | | |
|---|---|---|---|
| 1082752 | 9/1967 | United Kingdom | 607/30 |
| 1267046 | 3/1972 | United Kingdom | 607/9 |

OTHER PUBLICATIONS

Derwent's Abstract for Soviet Union Registration 1158-203, Published May 30, 1985.

Derwent's Abstract for Soviet Union Registration 641-966, Published Feb. 28, 1973.

*Primary Examiner*—William E. Kamm
*Assistant Examiner*—Kennedy J. Schaetzle
*Attorney, Agent, or Firm*—Hill, Steadman & Simpson

[57] ABSTRACT

A pacemaker contains at least one power-consuming component, such as a sensor with associated electronic circuitry for controlling the pacemaker function or a heart signal detector, and an electrode system for emitting heart stimulation pulses. The power-consuming component is disenabled prior to implantation of the pacemaker. Circuitry is provided for enabling the power-consuming component which is responsive to an event occurring substantially simultaneously with pacemaker implantation in the patient. Such circuitry may include a device for measuring the electrode impedance so as to enable the power-consuming component in response to the measured impedance value. The circuitry for enabling the power-consuming component can alternatively includes internal telemetry equipment in the pacemaker and external telemetry equipment for communications between the telemetry equipments. The external telemetry equipment can contain programming equipment and the internal telemetry equipment be arranged to enable the power-consuming component as soon as the programming equipment begins communicating at the time of implantation with the internal telemetry equipment, or by sending a special command from the programming equipment at the time of implantation. Alternatively the enabling circuitry can include a reed element, controllable by an external magnetic field, applied at the time of implantation, for enabling the power-consuming component.

10 Claims, 1 Drawing Sheet

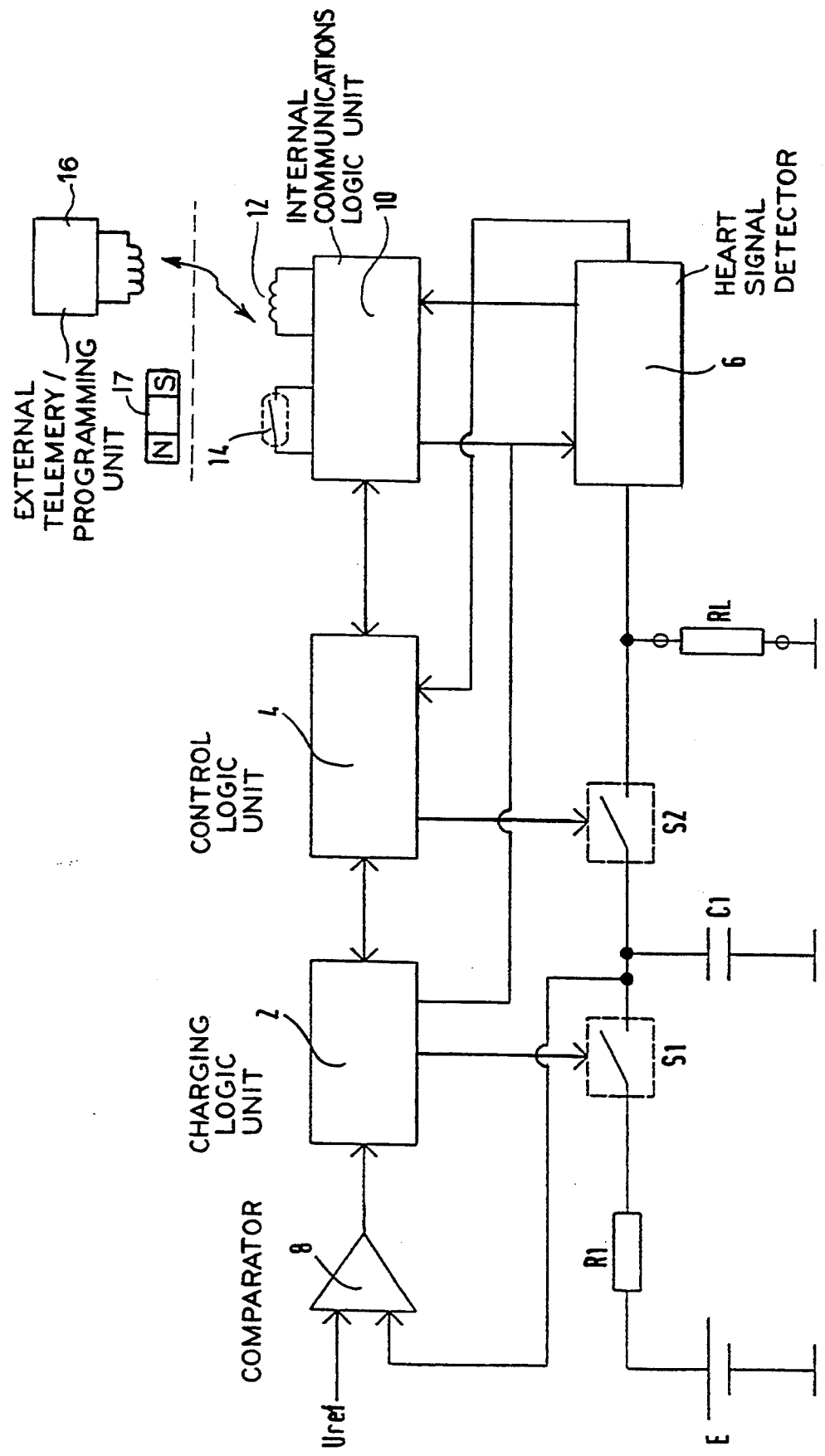

PACEMAKER WITH POWER-CONSUMING COMPONENT INHIBITED DURING STORAGE

BACKGROUND OF THE INVENTION

1. Field of the Invention

The present invention relates to a pacemaker of the type containing an electrode system for emitting heart stimulation pulses, and at least one power-consuming component connected to the pacemaker battery.

2. Description of the Prior Art

A typical pacemaker is operating and continuously emitting stimulation pulses from the time of its delivery from the factory.

Pacemakers have hitherto been delivered with even the heart signal detector or some other sensor already enabled at the factory. Since a pacemaker may be stored for up to 1 to 2 years prior to implantation, the heart signal detector or the sensor consumes power needlessly, thereby reducing the life of the pacemaker since it is drawing energy from the battery contained in the pacemaker.

SUMMARY OF THE INVENTION

An object of the present invention is to eliminate such needless power consumption and achieve a pacemaker which is delivered with a sensor or heart signal detector which is only enabled in conjunction with the pacemaker's implantation.

The above object is achieved in accordance with the principles of the present invention in an implantable pacemaker having a battery with at least one power-consuming component connected thereto, the power-consuming component being disenabled prior to implantation of the pacemaker, and means responsive to an event occurring substantially simultaneously with implantation of the pacemaker for enabling the power-consuming component.

The power-consuming component, for example, may be formed by sensor electronics which operate with a physiological sensor which is used to set the pacing rate, or may be a heart signal detector such as for detecting natural P-waves and/or R-waves.

The event occurring substantially simultaneously with the implantation of the pacemaker may be, for example, a significant change in impedance across the pacemaker electrodes, which may be measured directly or which may be measured indirectly by measuring a significant change in the charging time for the charging capacitor which is used to develop the voltage for a stimulation pulse, the external application of a magnetic field so as to close a reed switch in the implanted pacemaker, establishing a telemetry link between the implanted pacemaker and an external telemetry/programming unit, or a specific programming command transmitted telemetrically from the external programmer to the implanted pacemaker, all of which are discussed in more detail below.

Storage of the pacemaker with the heart signal detector or sensor disabled saves power with extended pacemaker life as a result.

If it is assumed that a pacemaker with associated sensor equipment draws a basic current of 4 $\mu$A during a storage period of 1 year and the invention reduces this power consumption by, e.g., a mere 1 $\mu$A, pacemaker operational life would increase by 3 months. However, the invention is capable of achieving even greater power savings.

In one embodiment of the pacemaker according to the invention, the means for enabling power-consuming component contain a device for measuring the electrode impedance so as to enable the sensor electronic circuitry when the impedance drops below a predesignated threshold value. In this way, automatic start-up of the sensor or heart signal detector is achieved when the pacemaker is implanted in the patient. Prior to implantation, the impedance of the electrode system is very high, so high that the impedance does not impose any load on the pacemaker. After the electrode system is connected to the heart, the impedance normally drops to about 500 ohms. Thus setting the threshold value for enabling sensor electronic circuitry, or the heart signal detector, at e.g., 2 kohms leaves a wide safety margin ensuring that sensor electronic circuitry, or the heart signal detector, is reliably activated at implantation.

In a further embodiment of the pacemaker according to the invention, in which stimulation pulses are generated by the discharge of a storage capacitor through an electrode system, the electrode impedance is measured with the aid of means for measuring the time required to recharge the reservoir capacitor to a predesignated stimulation voltage between each stimulation pulse. As noted above, the electrode system's impedance is very high before implantation. In this instance, discharge of the storage capacitor between two stimulation pulses is determined only by leakage currents in the capacitor itself and possibly in other components. Recharging of the reservoir capacitor to the predesignated stimulation voltage is therefore very fast. After implantation, however, the impedance of the electrode system is much lower, so a far bigger charge is discharged through the electrode system for each stimulation pulse. The time required to recharge the storage capacitor between two stimulation pulses is therefore much longer. Recharge time is normally less than 1 ms before implantation and in the 3-10 ms range after implantation.

In another embodiment of the pacemaker according to the invention, the storage capacitor is recharged in steps. Thus, charging takes place for a given period of time, and the storage capacitor's voltage is thereafter compared in a comparator to the predesignated stimulation voltage. If the capacitor voltage is less than the stimulation voltage, the capacitor is connected to the battery for additional charging for a second period of time. The capacitor voltage is then again compared to the predesignated stimulation voltage. This procedure is repeated until the capacitor voltage reaches or exceed the predesignated stimulation voltage, whereupon charging terminates. The periods of time in which the storage capacitor is connected to the battery during the recharging process are preferably of equal length, e.g., 1 ms.

In another embodiment of the pacemaker according to the invention, measurement of electrode impedance can be performed by a simple measurement of the voltage across the storage capacitor before and after emission of a stimulation pulse. Prior to pacemaker implantation, when the impedance of the electrode system is high, the difference in voltage before and after a stimulation pulse is relatively small, whereas this voltage difference is much bigger after the electrode system has been installed in the heart. The large drop in voltage measured during the stimulation pulse after implantation is used for enabling the sensor electronic circuitry or the heart signal detector.

Alternatively, the means for enabling the power-consuming component may include internal telemetry circuitry in the pacemaker and external telemetry circuitry for communications between the telemetry circuits. In this manner, the power-consuming component such as the sensor or the heart signal detector can be enabled extracorporeally, e.g., when the external telemetry circuitry contains programming circuits, and the internal telemetry circuitry is devised so that the sensor, or the heart signal detector, is enabled as soon as the programming equipment begins communicating with the internal telemetry equipment.

The programming circuit and the internal telemetry circuitry are then constructed such that the sensor electronics or heart signal detector is only enabled when communication is established exactly between the actual pacemaker and its associated programming circuit. Non-communicating use of the programming circuit will not enable the sensor or heart signal detector in question. Alternatively, the sensor or the heart signal detector can be enabled with a special programming command.

In yet another alternative embodiment of the pacemaker according to the invention, the means for enabling the power-consuming component contains a reed element switch, controllable by an externally applied magnetic field, for enabling the sensor electronic circuitry or the heart signal detector, e.g., by application of a magnet in the vicinity of the pacemaker.

If the pacemaker is a dual chamber design with two heart signal detectors, means according to the invention can be provided to enable each detector at the time the pacemaker is implanted. Thus, the inventive idea can be used to advantage even in dual chamber pacemakers.

DESCRIPTION OF THE DRAWINGS

The single figure is a schematic block diagram of the basic components of a pacemaker having various enabling means constructed in accordance with the principles of the present invention.

DESCRIPTION OF THE PREFERRED EMBODIMENTS

In order to produce stimulation pulses with an appropriate amplitude to the heart, a storage capacitor C1 is charged to a predesignated stimulation voltage by connecting the capacitor C1 to the battery E via a resistor R1 with the switch SI. When the voltage of capacitor C1 exceeds the predesignated stimulation voltage, the switch S1 opens and terminates recharging. The switch S1 is controlled by a recharge logic unit 2.

When a stimulation pulse is delivered to the heart, represented in the drawing as an impedance RL, the switch S2 closes for a brief time so the storage capacitor C1 is discharged across electrodes 15 and through heart impedance RL. The switch S2 is controlled by a control logic unit 4.

Capacitor C1 is discharged in proportion to the magnitude of the heart impedance RL as "seen" by the electrodes 15.

Prior to pacemaker implantation, the impedance RL of the electrode system is very high, so the pacemaker does not sense any load, and discharge of the reservoir capacitor C1 is determined by leakage currents in the capacitor itself and other components.

When the pacemaker is implanted and the electrode system is applied in the heart, the magnitude of the impedance RL drops drastically. This drop in impedance is used for enabling the heart signal detector 6.

The impedance RL can be measured in different ways.

Since the magnitude of the charge emitted through the impedance RL is governed by the magnitude of the impedance, the impedance can be determined by measuring the time required to recharge the reservoir capacitor C1 between each stimulation pulse, i.e., the time the switch S1 must be closed to recharge the capacitor C1 to the predesignated stimulation voltage.

After a stimulation pulse has been delivered and the switch S2 has opened, the switch S1 closes, and recharging of the storage capacitor C1 begins. A comparator 8 compares the voltage (or a voltage - divided portion) of the capacitor C1 to a reference voltage Uref, corresponding to the predesignated stimulation voltage. When the voltage in the capacitor C1 reaches the value Uref, the comparator 8 sends a signal to the charging logic unit 2 which opens the switch SI. The capacitor C1 is then ready to emit a new stimulation pulse.

As noted above, the impedance RL is very high before pacemaker implantation, so the capacitor C1 only loses a very small part of its charge between the stimulation pulses, and the recharge time is short in this instance, i.e., less than 1 ms. After pacemaker implantation, the impedance RL is much lower, and the time required to recharge the capacitor C1 is much longer. Thus, this difference in recharging time constitutes a measure of the impedance RL in the heart electrode system, and the signal detector 6 is enabled when recharging time becomes sufficiently long. The limit value for enabling the heart signal detector 6 is normally in the 3–10 ms range. The actual recharging time after the pacemaker has been implanted is usually longer, so the heart signal detector 6 can be safely enabled as soon as the pacemaker and electrode system have been implanted.

Recharging of the storage capacitor C1 can, e.g., occur in steps, so the switch S1 is closed for a fixed period of time, e.g., 1 ms, and opens thereafter, the capacitor voltage is compared to the reference voltage Uref and the switch S1 then re-closes once again for 1 ms if the capacitor voltage is less than Uref. A new comparison to Uref is made 1 ms later, and the process continues until the capacitor voltage reaches or exceeds the reference voltage Uref, recharging then terminating. The number of recharge periods required to achieve the reference voltage is a measure of the charge fed to the reservoir capacitor C1 and thus is also a measure of the impedance RL. In this procedure, the charging logic unit 2 contains a clock for supplying the requisite time base.

When the electrode system has been connected, the magnitude of the load impedance RL is about 500 ohms. Setting the limit value for enabling the heart signal detector 6 at, e.g., 2 kohms leaves a wide margin of safety.

In one practical embodiment, the different components can have the following numerical values:
Battery voltage, $E=2.8$ V
Resistor, $RI=2.5$ kohms
Capacitor, $CI=10$ $\mu$F
Reference voltage, $Uref=2.4$ V The capacitor C1 discharges through the impedance RL for 1 ms. When $RL=2$ kohms, the voltage across the capacitor C1 drops in stimulation with about 117 reV. The switch S1 must thereafter remain closed for about 6.4 ms for the capacitor C1 to recharge to Uref=2.4 V.

If the pacemaker is assumed to be implanted and the electrode impedance RL is less than 2 kohms, the heart signal detector 6 is enabled if the voltage difference across capacitor C1 exceeds 117 mV or if the capacitor recharging time exceeds 6.4 ms.

One alternative way of measuring electrode impedance RL in order to establish when the heart signal detector 6 should be enabled is to measure the difference in capacitor voltage before and after stimulation, i.e., before and after closure of the switch S2. Since the voltage difference increases with decreasing impedance RL, measurement of this voltage makes it possible to determine when the heart signal detector 6 should be enabled.

In another embodiment of the pacemaker according to the invention, the heart signal detector 6 can be enabled by telemetric means, either immediately before or after implantation. To this end, this embodiment of the pacemaker according to the invention contains communications logic unit 10 with a telemetry coil 12 for communications with an external telemetry/programming unit 16 by means of which the heart signal detector 6 can also be enabled. The heart signal detector 6 can be automatically enabled so it turns on as soon as the programming unit 16 begins telemetrically communicating with the pacemaker, or the heart signal detector 6, can be enabled with a special programming command. In the first case the programming unit 16 thus has a protocol adapted to the associated pacemaker, such that the sensor is enabled as soon as a communication channel is established between the programming unit 16 and the pacemaker (possibly including an answer-back from the pacemaker). Turning on programming equipment which is not intended for the pacemaker in question does not however, result in enabling of the sensor or heart signal detector.

In another version of the pacemaker according to the invention, the communications logic unit 10 is equipped with a reed element 14, controllable by an externally applied magnetic field from a magnet 17, for enabling the heart signal detector 6 immediately before or after implantation.

The invention has been described above as applied to a single chamber pacemaker. However, the invention can be applied with advantage to a dual chamber pacemaker with two heart detectors.

The invention idea can even be utilized with other pacemaker functions, such as sensor electronic circuitry for controlling pacemaker function with sensors, e.g., piezoelectric movement or activity sensors, accelerometers and oxygen sensors, which should not be enabled until the pacemaker is implanted. Such pacemakers are thus often equipped with runaway protection preventing the pacing rate from becoming too fast. This runaway protection can also be disabled to advantage until the time of pacemaker implantation in order to save power and thereby extend battery and pacemaker life.

It will be understood that the pacemaker shown in the drawing, for explanatory purposes, includes more than one enabling means. In practice, only one such enabling means is needed, although more than one may nonetheless be provided for redundancy.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable pacemaker comprising:
    a battery;
    at least one power-consuming component connected to said battery, said power-consuming component being disenabled prior to implantation of said pacemaker;
    electrodes adapted for in vivo delivery of electrical energy from said battery to a patient, said electrodes having an having an impedance across said electrodes; and
    means responsive to a predetermined change in said impedance occurring substantially simultaneously with implantation of said pacemaker for enabling said power-consuming component.

2. An implantable pacemaker as claimed in claim 1 wherein said means for enabling said power-consuming component includes means for directly measuring said impedance.

3. An implantable pacemaker as claimed in claim 1 further comprising means for generating a series of stimulation pulses by alternating charging and discharging of a storage capacitor, and wherein said means for enabling said power-consuming component includes means for measuring a time required to charge said storage capacitor, after discharge of said capacitor, to a predetermined voltage.

4. An implantable pacemaker as claimed in claim 1 further comprising:
    means for generating a stimulation pulse by charging and discharging a storage capacitor including a switch connected between said capacitor and said battery;
    means for controlling operation of said switch to close said switch for a plurality of successive periods;
    comparator means for comparing the voltage across said capacitor after each closure of said switch to a reference voltage and for supplying a signal to said means for closing said switch to close said switch for another period repeatedly until said voltage across said capacitor equals or exceeds said reference voltage; and
    wherein said means for enabling said power-consuming component comprises means for enabling said power-consuming component when the sum of said periods exceeds a predetermined value.

5. An implantable pacemaker as claimed in claim 4 wherein said means for closing said switch comprises means for closing said switch for a plurality of successive equal periods.

6. An implantable pacemaker as claimed in claim 1 further comprising pulse generator means for generating stimulation pulses by charging and discharging a storage capacitor, and wherein said means for measuring said impedance comprises means for measuring the voltage across said storage capacitor before and after emission of a stimulation pulse.

7. An implantable pacemaker as claimed in claim 1 wherein said at least one power-consuming component comprises at least one heart signal detector means for detecting natural heart signals.

8. An implantable pacemaker as claimed in claim 1 wherein said at least one power-consuming component comprises a sensor and circuitry for operating said sensor for detecting a physiological parameter of a patient in whom said pacemaker is implanted.

9. An implantable pacemaker for use with an external telemetry unit, said pacemaker comprising:
   a battery;
   at least one power-consuming component connected to said battery, said power-consuming component being disenabled prior to implantation of said pacemaker;
   internal means contained in said pacemaker for telemetrically communicating with said external telemetry unit; and
   means responsive to an establishment of a telemetry link between said internal means and said external telemetry unit occurring substantially simultaneously with implantation of said pacemaker for enabling said power-consuming component.

10. An implantable pacemaker for use with an external programmer which generates a predetermined program command, said implantable pacemaker comprising:
   a battery;
   at least one power-consuming component connected to said battery, said power-consuming component being disenabled prior to implantation of said pacemaker;
   implanted telemetry means contained in said pacemaker for communicating by telemetry with said external programmer; and
   means responsive to receipt of said predetermined program command from said external programmer by said implanted telemetry means occurring substantially simultaneously with implantation of said pacemaker for enabling said power-consuming component.

* * * * *